United States Patent
Rahaman et al.

(10) Patent No.: US 12,128,497 B2
(45) Date of Patent: Oct. 29, 2024

(54) LASER FOCAL SPOT SIZE MEASUREMENT USING A BUILT-IN CAMERA FOR AN OPHTHALMIC LASER SYSTEM

(71) Applicant: AMO Development, LLC, Irvine, CA (US)

(72) Inventors: Mohammad Saidur Rahaman, Santa Clara, CA (US); Hong Fu, Pleasanton, CA (US)

(73) Assignee: AMO Development, LLC, Irvine, CA (US)

( * ) Notice: Subject to any disclaimer, the term of this patent is extended or adjusted under 35 U.S.C. 154(b) by 444 days.

(21) Appl. No.: 17/450,452

(22) Filed: Oct. 8, 2021

(65) Prior Publication Data

US 2022/0118550 A1   Apr. 21, 2022

Related U.S. Application Data

(60) Provisional application No. 63/093,117, filed on Oct. 16, 2020.

(51) Int. Cl.
| | |
|---|---|
| *A61F 9/008* | (2006.01) |
| *A61B 3/10* | (2006.01) |
| *A61B 3/14* | (2006.01) |
| *B23K 26/073* | (2006.01) |

(52) U.S. Cl.
CPC .......... *B23K 26/073* (2013.01); *A61B 3/1025* (2013.01); *A61B 3/14* (2013.01); *A61F 9/00802* (2013.01); *A61F 2009/00897* (2013.01)

(58) Field of Classification Search
CPC ....... B23K 26/073; A61B 3/1025; A61B 3/14; A61F 2009/00897; A61F 9/00802

USPC ............................................................ 606/4
See application file for complete search history.

(56) References Cited

U.S. PATENT DOCUMENTS

| | | | |
|---|---|---|---|
| 4,917,489 A  * | 4/1990 | Nishio | G01J 1/4257 |
| | | | 356/121 |
| 5,029,220 A | 7/1991 | Juday | |
| 6,287,299 B1 | 9/2001 | Sasnett et al. | |
| 7,982,169 B2 | 7/2011 | Kittelmann et al. | |
| 9,022,037 B2 | 5/2015 | Delfyett et al. | |

(Continued)

FOREIGN PATENT DOCUMENTS

| | | | | |
|---|---|---|---|---|
| JP | 4057311 B2 * | 3/2008 | ............ | B23K 26/04 |
| JP | 2014522284 A * | 9/2014 | | |
| WO | WO-2014163891 A1 * | 10/2014 | ........... | A61B 3/1015 |

*Primary Examiner* — Michael J Lau
(74) *Attorney, Agent, or Firm* — Johnson & Johnson Surgical Vision, Inc.

(57) ABSTRACT

An ophthalmic laser surgical system has a built-in imaging sensor for measuring laser focal spot size. An objective lens focuses the laser beam to a focal spot near a reflective surface, scans the focal spot in the depth direction, and focuses light reflected by the reflective surface to form a back-reflected light. A two-dimensional imaging sensor receives a sample of the back-reflected light to generate images of the back-reflected light. During the depth scan, the image contains a well-focused light spot when the laser focal spot is located at a fixed offset distance before the reflective surface, but the light spot in the images is otherwise defocused. The images generated during the scan are analyzed to find the smallest light spot size among the images. The laser focal spot size is then calculated from the smallest light spot size using a magnification factor which is a system constant.

13 Claims, 2 Drawing Sheets

(56) References Cited

U.S. PATENT DOCUMENTS

| | | |
|---|---|---|
| 9,603,519 B2 | 3/2017 | Bor et al. |
| 10,105,260 B2 | 10/2018 | Raksi |
| 10,179,070 B2 | 1/2019 | Berezhnyy et al. |
| 2001/0056276 A1 | 12/2001 | Lahaye et al. |
| 2003/0193647 A1* | 10/2003 | Neal ........................ A61B 3/14 351/221 |
| 2009/0131921 A1 | 5/2009 | Kurtz et al. |
| 2009/0171325 A1 | 7/2009 | Koenig |
| 2009/0247997 A1 | 10/2009 | Watanabe et al. |
| 2012/0310141 A1* | 12/2012 | Kornfield .............. A61F 9/0008 604/20 |
| 2013/0072917 A1* | 3/2013 | Kaschke ............ A61F 9/00736 606/6 |
| 2014/0104576 A1* | 4/2014 | Bor .......................... A61B 3/10 351/215 |
| 2015/0141972 A1* | 5/2015 | Woodley ............ G01B 9/02091 606/5 |
| 2018/0339363 A1* | 11/2018 | Lee ...................... B23K 26/048 |
| 2020/0011659 A1 | 1/2020 | Sun et al. |
| 2020/0064622 A1* | 2/2020 | Rahaman ................ A61F 9/008 |
| 2020/0116897 A1* | 4/2020 | Schadlu ................. G16H 80/00 |
| 2020/0289318 A1* | 9/2020 | Liu ..................... A61F 9/00827 |

\* cited by examiner

LASER FOCAL SPOT SIZE MEASUREMENT USING A BUILT-IN CAMERA FOR AN OPHTHALMIC LASER SYSTEM

CROSS-REFERENCE TO RELATED APPLICATIONS

This application claims the benefit under 35 U.S.C. § 119(e) of U.S. Provisional Patent Application No. 63/093,117, filed Oct. 16, 2020, which is incorporated herein by reference in its entirety.

BACKGROUND OF THE INVENTION

Field of the Invention

This invention relates to ophthalmic laser surgical systems, and in particular, it relates to a laser focal spot size measurement system and method for ophthalmic laser surgical systems.

Description of Related Art

Ophthalmic laser surgical systems use a laser device to generate a pulsed or continuous laser beam, and use a beam delivery optical system to focus the laser beam to a highly focused spot and deliver the laser focal spot in target tissues of the eye to effectuate various types of treatments of the eye. In many laser ophthalmic surgical systems, the laser device generates a pulsed laser beam having ultra-short pulse lengths in the range of femtoseconds to nanoseconds, and the beam is focused to a focal spot size as small as 1 µm or less. A scanning device of the beam delivery system scans the laser focal spot inside the eye tissue to form incisions in the tissue. In such laser surgical systems, the laser focal spot size in the eye is a critical parameter that determines the tissue incision quality such as precision of the incision. Spot size is also a critical parameter for designing laser spot scan patterns that avoid collateral damage to eye tissues to ensure patient safety. Unintended movements of optical elements in the laser beam path can lead to misalignment of the beam and thus, spot size change. The change in sport size reduces tissue cutting energy density at the focal spot in a quadratic manner. Therefore, measuring the laser focal spot size is important.

In conventional ophthalmic laser surgery systems, the laser focal spot size can be determined either by directly measuring it using a spot size camera, where the laser beam shines on the camera (with or without additional optical elements in front of the camera), or by indirectly deriving it from wavefront measurements of the light beam. For example, commonly owned U.S. Pat. Appl. Pub. No. 2020/0011659 describes a spot size camera built in combination with a water immersed objective lens. The water immersed objective lens collects the laser beam after the focal spot and collimates it towards the camera plane with a fix magnification. Systems employing external spot size cameras may be used for troubleshooting and laser system health checkup, but is difficult to use in connection with actual ophthalmic surgery.

SUMMARY

There is a need for an ophthalmic laser surgical system that incorporates an automatic and built-in measurement system for measuring and monitoring the laser focal spot size. Such feature will simplify the optical system performance diagnose and enable remote monitoring of optical performance.

An object of the present invention is to provide a built-in spot size measurement capability which can allow remote access of the spot size data and allow for convenient laser system health check up remotely at regular intervals.

Another object of the present invention is to provide real-time laser focal spot size monitoring as a laser beam quality indicator.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides an ophthalmic laser system which includes: a laser device configured to generate a laser beam; an optical system including a moveable objective lens configured to focus the laser beam to a focal spot and to scan the focal spot in a depth direction which is parallel to an optical axis of the objective lens, and to focus a reflected portion of the laser beam that has been reflected by a reflective surface disposed in front of the objective lens to form a back-reflected laser beam; a two-dimensional imaging sensor disposed to capture a two-dimensional image of the back-reflected laser beam; and a controller electrically coupled to the laser device, the optical system and the imaging sensor, wherein the controller is configured to: control the laser device to generate a laser beam; control the optical system to scan a focal spot of the laser beam in the depth direction within a predetermined depth range; control the imaging sensor to capture a plurality of images of the back-reflected laser beam while the focal spot of the laser beam is scanned within the depth range; analyze the plurality of captured images to measure a smallest light spot size among the plurality of captured images; and calculate a size of the focal spot of the laser beam using the measured smallest light spot size and a predetermined magnification factor.

In another aspect, the present invention provides a method implemented in an ophthalmic laser system for measuring a laser focal spot size, which includes: mounting a patient interface device on a housing of the ophthalmic laser system; by a laser device of the ophthalmic laser system, generating a laser beam; by an objective lens of the ophthalmic laser system, focusing the laser beam to a focal spot and scanning the focal spot in a depth direction within a predetermined depth range, the depth direction being parallel to an optical axis of the objective lens; by the objective lens, focusing a reflected portion of the laser beam that has been reflected by a reflective surface of the patient interface device to form a back-reflected beam; by a two-dimensional imaging sensor of the ophthalmic laser system, receiving the back-reflected beam and capturing a plurality of images of the back-reflected beam while the focal spot is scanned within the depth range; by a controller of the ophthalmic laser system, analyzing the plurality of captured images to measure a smallest light spot size among the plurality of captured images; and by the controller, calculating a size of the focal spot of the laser beam using the measured smallest light spot size and a predetermined magnification factor.

In some embodiments, the predefined depth range includes a depth located at an offset distance before the reflective surface, wherein the offset distance is a fixed value determined by a focal length of the objective lens and a length of an optical path from the imaging sensor to the objective lens.

In some embodiments, the predetermined magnification factor is a fixed value determined by a focal length of the objective lens and a length of an optical path from the imaging sensor to the objective lens.

In some embodiments, the system further includes: a housing, configured to contain at least the objective lens of the optical system; and a patient interface device mounted on the housing, wherein the reflective surface is a surface of a lens of the patient interface device.

It is to be understood that both the foregoing general description and the following detailed description are exemplary and explanatory and are intended to provide further explanation of the invention as claimed.

DETAILED DESCRIPTION OF PREFERRED EMBODIMENTS

Embodiments of the present invention provides a laser beam delivery system for an ophthalmic laser surgical system which incorporates a built-in laser focal spot size measurement system, which allows for real-time laser focal spot size measurement and monitoring and allows for remote access of the laser focal spot size data.

Figure 1:
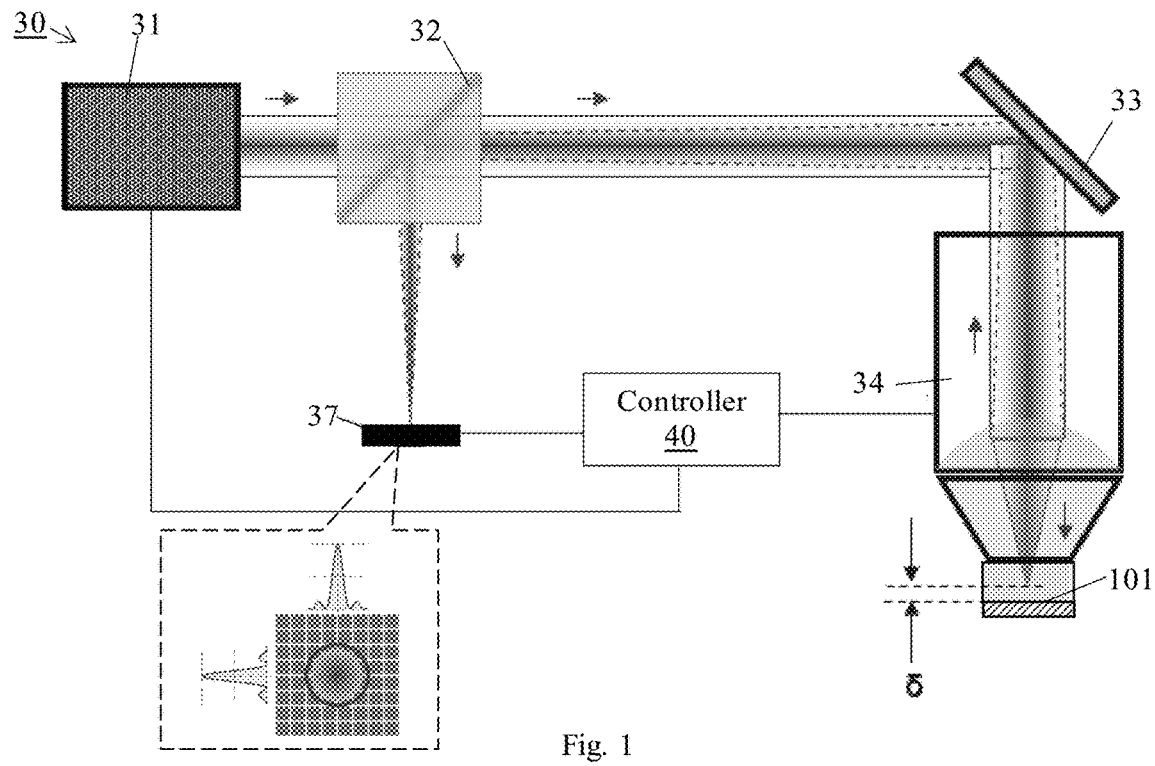
FIG. 1 schematically illustrates a laser beam delivery system for an ophthalmic laser surgical system which incorporates a built-in focal spot size camera according to an embodiment of the present invention.

FIG. 1 schematically illustrates a portion of an ophthalmic laser system 30 that employs a built-in spot size camera according to an embodiment of the present invention. In the system shown in FIG. 1, the laser source 31, the details of which are not shown, includes a laser device and associated optical components, configured to produce a laser beam. A part of the laser beam passes through a beam splitter 32, and after being reflected by one or more mirrors 33 (optional, and may be XY scanning mirrors), is focused by the objective lens 34. In a preferred embodiment, the objective lens 34 has a relatively high numerical aperture (NA), for example, approximately 0.4 or higher.

The objective lens 34 is mounted on a movement structure and moveable in the Z direction (parallel to the optical axis) relative to a housing of the laser system, so as to focus the laser beam at desired depths and to vary the depth of the focal spot. The movement structure may include any suitable mechanical structure, such as a translation stage driven by a motor, etc.

A part of the laser light that exits the objective lens 34 is reflected by a reflective interface 101 located below the objective lens 34, and the reflected light travels backwards into the objective lens 34. The reflective interface 101 may be, for example, a surface of a contact lens of a patient interface device (a device used in ophthalmic procedures to mechanically couple the patent's eye to the laser system) which is mounted on the housing. After the back-reflected light is focused by the objective lens 34 and reflected by the mirror 33, a part of the reflected light is directed by the beam splitter 32 onto a two-dimensional imaging sensor 37 (e.g. a CCD or CMOS imaging sensor, etc.) and captured by the imaging sensor. In preferred embodiments, no other lenses are used in front of the imaging sensor 37 or anywhere else between the objective lens 34 and the imaging sensor. In other words, the image is formed by the objective lens on the light detecting surface of the imaging sensor.

A controller 40 controls the operations of the laser source 31, objective lens 34, and imaging sensor 37. The controller may be implemented by electrical circuitry including logic circuits, and/or processors which execute computer executable program code stored in computer readable non-volatile memories.

Figure 2A:
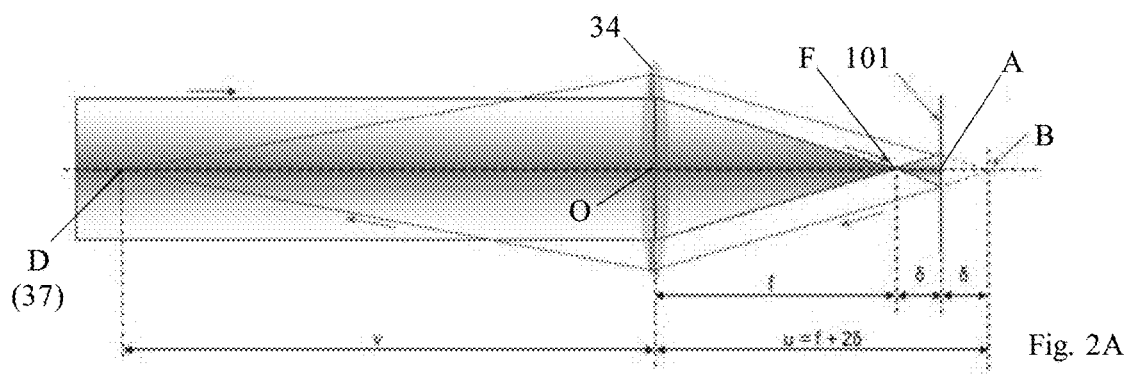
FIGS. 2A and 2B schematically illustrate the principle of laser focal spot size measurement in the system of FIG. 1.
Figure 2B:
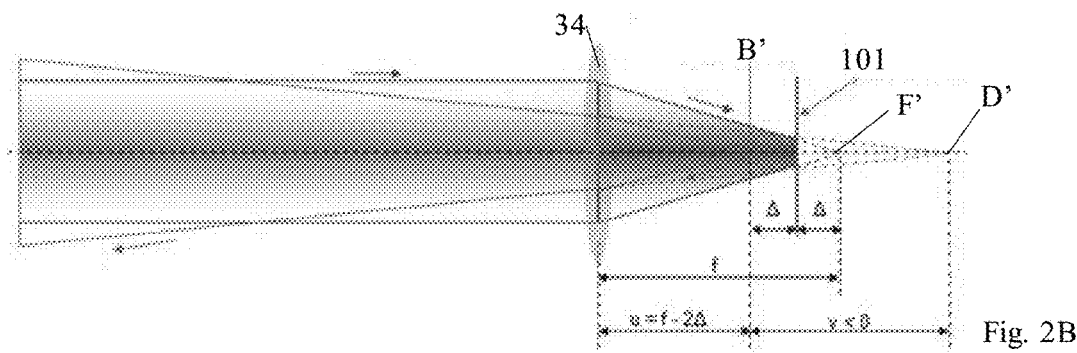

The principle of laser focal spot size measurement using the system of FIG. 1 is described below with reference to the schematic illustrations in FIGS. 2A and 2B. In FIGS. 2A and 2B, the objective lens 34 is optically represented by a thin lens having a focal distance f, although the objective lens is typically formed of a set of lenses. It should be noted that FIGS. 2A and 2B are intended to explain the relevant optical principles; the various distances depicted in the figures are not to scale.

FIG. 2A illustrates a situation where the objective lens 34 focuses the parallel incident beam to a focus point F located between the objective lens 34 and the reflective interface 101. In other words, the reflective interface 101 is located beyond the focal plane of the objective lens 34. The forward propagating light diverges after the focus point F and is then reflected by the reflective interface 101. To the objective lens 34, the reflected light appears to originate from a point B behind the reflective interface 101, the point B being the mirror image of the focus point F with respect to the reflective interface 101. Because the actual laser focal spot at the focus point F has a finite lateral size (which is the laser focal spot size being measured), its mirror image at point B also has a finite lateral size, i.e., the reflected light appears to originate from a real object of a finite size (which is equal to the laser focal spot size being measured) located at an object plane at position B. The distance from the equivalent origin B to the objective lens 34 is $u=f+2\delta$ (Equation (1)), where $\delta=FA$ is the offset distance between the focus point F and the reflective interface 101. The reflected light, which appears to originate from the object plane at position B, is focused by the objective lens 34 to an image plane D located at a finite distance v from the objective lens. The imaging sensor 37 is located at the image plane D, and no other lens is disposed between the objective lens 34 and the imaging sensor 37.

Using Equation (1) and the following lens formula for a thin lens (Equation (2)), $$\frac{1}{u} + \frac{1}{v} = \frac{1}{f},$$

where u is the object distance and v is the image distance, one obtains (Equation (3)):

$$\delta = \frac{f^2}{2(v-f)}$$

When f is much smaller than v (discussed later), one obtains (Equation (4)):

$$\delta \approx \frac{f^2}{2v}$$

The above equations are for focusing in the air. If the focus point F is located inside an optical medium other than air, the refractive index n of the optical medium is taken into consideration, and one obtains (Equation (5)):

$$\delta \approx n \cdot \frac{f^2}{2v}$$

It should be understood that in the above equations, the various distances are the distances along the optical path; the optical path may be folded by mirrors or beam splitters.

In the laser system 30, the distance DO from the imaging sensor 37 to the objective lens 34 (i.e. the imaging distance v) is approximately a system constant, because the location of the imaging sensor 37 is fixed relative to the laser system housing and the amount of focusing movement of the objective lens 34 with respect to the housing is much smaller than the distance DO. Therefore, the offset distance δ given by Equation (5) is approximately a constant of the laser system 30. The point located at distance δ before the reflective interface 101 is referred to as the target focus position for convenience. If the light is focused by the objective lens 34 at this target focus position, the reflected light from the reflective interface 101 will be focused onto the imaging sensor 37.

In some embodiments, the focal length f, i.e. the equivalent focal length of the objective lens 34, is a few mm, e.g. approximately 4 mm. Meanwhile, the distance DO from the imaging sensor 37 to the objective lens 34 may be several hundreds of mm, because the choice of the imaging sensor location is not constrained and the image distance v may be lengthened if desired by folding the optical path with mirrors. Therefore, f is much smaller than v (by a factor on the order of 100). In one particular embodiment, where the image distance v (DO) is approximately 724.9 mm and the focal length f is 3.92 mm, and when the focal spot is located in air, Equation (5) gives δ≈21 μm.

When the objective lens 34 focuses the laser beam at positions other than the target focus position defined by the offset δ, the back-reflected light will not be focused on the imaging sensor 37 located at plane D, but will be focused before it, after it, or not be focused at all. FIG. 2B schematically illustrates an example where the focus point F' of the objective lens 34 is located beyond the reflective interface 101. The light from the objective lens 34 converges as it strikes the reflected interface 101 and is reflected by it; therefore, to the objective lens 34, the back-reflected light appears to originate from a point B' before the reflective interface 101, the point B' being the mirror image of the focus point F' with respect to the reflective interface 101. Since the distance from the point B' to the objective lens 34 is shorter than the focal distance, the back-reflected light remains divergent after it passes through the lens 34. As illustrated in FIG. 2B, the distance from the focus point F' to the reflective interface 101 is denoted Δ; the back-reflected light has an object distance u=f−2Δ, and forms a virtual image at a point D' behind the lens 34.

To summarize, the back-reflected light from the reflective interface 101 will only form a well focused real image on the imaging sensor 37 when the objective lens 34 focuses the parallel incident beam to the target focus position defined by the offset δ (Equation (5)).

Figure 3:
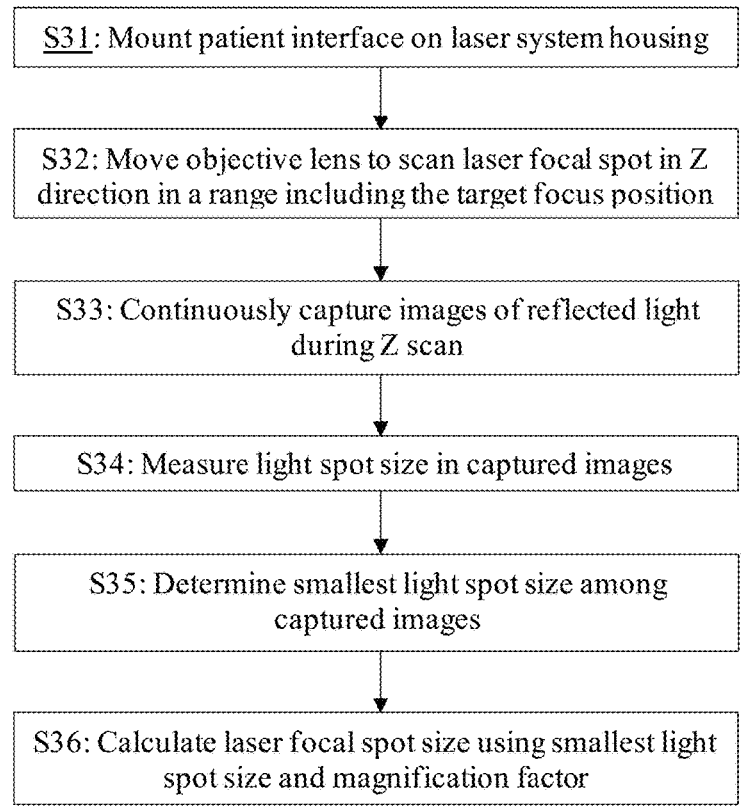
FIG. 3 schematically illustrates a laser focal spot size measurement method using the system of FIG. 1.

To measure the laser focal spot size (see FIG. 3), after the patient interface device (having the reflective interface) is mounted on the laser system housing (step S31), the controller 40 controls the objective lens 34 (via its movement structure) to scan the Z position of the laser focal spot in a depth range that includes the target focus position (step S32). In practice, the position of the reflective surface, such as the surface of the contact lens of the patient interface device, is approximately known, so an appropriate depth range may be estimated based on the estimated position of the reflective surface. During the scan, the controller also controls the imaging sensor 37 to continuously capture images (step S33).

Figure 4:
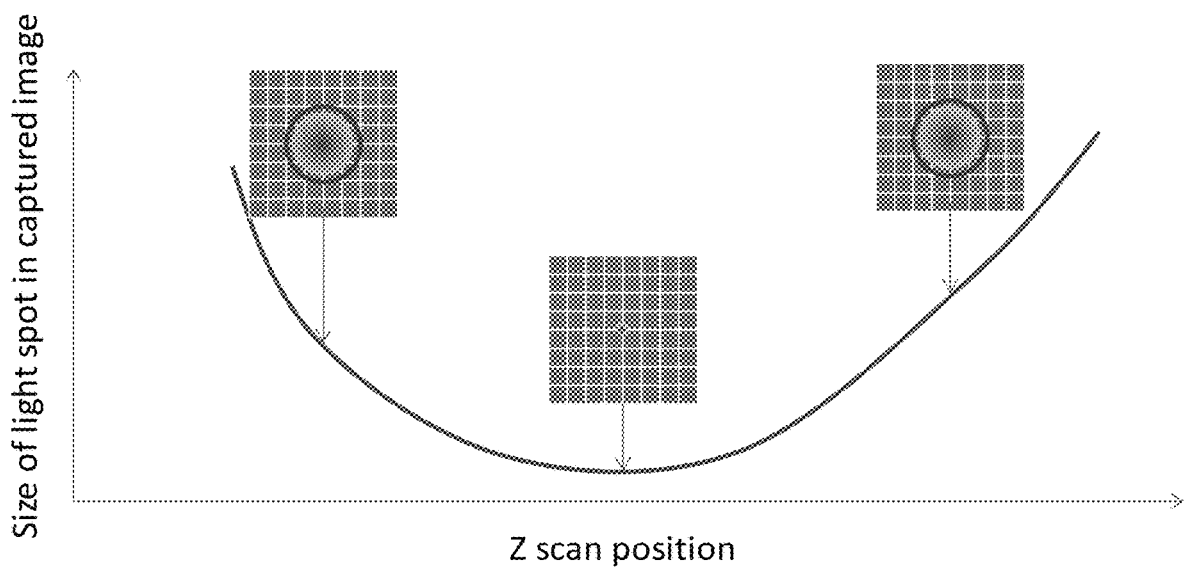
FIG. 4 schematically illustrates a relationship between the light spot size in captured images and the Z scan position in the method of FIG. 3.

As explained earlier, when the laser focal spot is located at the target focus position, the laser focal spot (after reflection by the reflective surface) is focused on the imaging sensor 37, so the image captured by the imaging sensor contains a well focused light spot; when the laser focal spot is located away from the target focus position, the images captured by the imaging sensor contain a defocused light spot. Therefore, the size of the light spot in the captured image changes as the laser focal spot is scanned in the Z direction. The smallest light spot among the capture images occurs when the laser focal spot is located at the target focus position, and the light spot size increases as the Z position moves away from the target focus position. FIG. 4 schematically illustrates a relationship between the light spot size in the captured image and the Z scan position during a Z scan, showing the light spot image going in and out of focus. Here, the Z scan position may be a position relative to a reference position defined by the outer housing 20, or it may simply be a parameter of the objective lens movement structure; the actual value of the Z scan position is not important for the purposes of focal spot size measurement.

The controller calculates the spot size of the light spot in the captured images (step S34), for example, by measuring the full width at half maximum (FWHM) of the two-dimensional light intensity profile. The imaging sensor should have sufficient pixel resolution to provide an accurate measure of the light spot size.

The controller further determines the smallest size of the light spot among the images (step S35). This smallest light spot size, which corresponds to the condition where the laser beam is focused at the target focus position, is then used to calculate the size of the laser focal spot using a known magnification factor (step S36). As shown in FIG. 2A, when the laser beam is focused at the target focus position, the object distance is u=f+2δ and the magnification factor is therefore v/u=v/(f+2δ) (Equation (6)). The magnification factor may also be directly calculated from the lens formula: v/u=v/f−1 (Equation (7)). As described earlier, v, f and δ are system constants; therefore, the magnification factor v/u is a system constant. The laser focal spot size is the size of the smallest light spot in the captured images divided by the magnification factor.

Using the values in the particular example described earlier, the magnification factor is v/u=724.9 mm/3.941 mm≈183.9. This magnification factor shows that, if the actual laser focal spot size is about 1 μm, the light spot size at the imaging plane is about 184 μm, which can be well resolved by a CCD or CMOS imaging sensor. This high magnification factor improves the accuracy of the focal spot size measurement.

The laser focal spot size measurement system and method described above provides many practical advantages. Because no external measurement tools are needed except the patient interface device, which can be easily installed onto the laser system, the measurement operation is easy and convenient. The system is also cost effective and robust.

As the laser focal spot size is an important indication of the condition of the laser system and the overall alignment of the beam delivery optical system, this focal spot size measurement system and method may be used to perform regular (e.g. daily) spot size monitoring. The operation may be performed from a remote location via the controller, and the measurement result may be remotely accessed to provide an indicator of laser system conditions.

Due to its convenience, the laser focal spot size measurement may be performed at times very close to an actual ophthalmic procedure on a user. For example, the spot size measurement may be performed immediately before the ophthalmic procedure. It may even be performed while the patient's eye is engaged with the patient interface device (in such applications, the laser pulse energy will be reduced to a level safe for the eye). These applications may be considered real-time applications.

In addition to laser focal spot size measurement, the light spot images captured by the imaging sensor may be used to measure the transverse (XY) center position of the beam (i.e. the mechanical and optical beam center). This is useful for centration in corneal lenticule extraction procedures, or for detecting overall XY misalignment of the system. Changes in alignment in the optical system can be detected using such a method. This method can also be used to detect tilt of the patient interface, because such tilt will cause the center of the light spot in the captured image to change.

It will be apparent to those skilled in the art that various modification and variations can be made in the built-in laser focal spot size measurement system and method of the present invention without departing from the spirit or scope of the invention. Thus, it is intended that the present invention cover modifications and variations that come within the scope of the appended claims and their equivalents.

What is claimed is:

1. An ophthalmic laser system comprising:
   a laser device configured to generate a laser beam;
   an optical system including a moveable objective lens and a reflective surface disposed in front of the objective lens, the reflective surface being a planar surface other than a surface of an eye of a subject, wherein the objective lens is configured to focus the laser beam to a focal spot and to scan the focal spot in a depth direction which is parallel to an optical axis of the objective lens, and to focus a reflected portion of the laser beam that has been reflected by the reflective surface to form a back-reflected laser beam;
   a two-dimensional imaging sensor disposed to capture a two-dimensional image of the back-reflected laser beam; and
   a controller electrically coupled to the laser device, the optical system and the imaging sensor, wherein the controller is configured to:
   control the laser device to generate a laser beam;
   control the optical system to scan a focal spot of the laser beam in the depth direction within a predetermined depth range;
   control the imaging sensor to capture a plurality of images of the back-reflected laser beam while the focal spot of the laser beam is scanned within the depth range;
   analyze the plurality of captured images to measure a smallest light spot size among the plurality of captured images; and
   calculate a size of the focal spot of the laser beam using the measured smallest light spot size and a predetermined magnification factor.

2. The ophthalmic laser system of claim 1, wherein the predefined depth range includes a depth located at an offset distance before the reflective surface, wherein the offset distance is a fixed value determined by a focal length of the objective lens and a length of an optical path from the imaging sensor to the objective lens.

3. The ophthalmic laser system of claim 1, wherein the predetermined magnification factor is a fixed value determined by a focal length of the objective lens and a length of an optical path from the imaging sensor to the objective lens.

4. The ophthalmic laser system of claim 1, wherein the controller is configured to measure a light spot size in each captured image by measuring a full width at half maximum of a two-dimensional light intensity profile in the captured image.

5. The ophthalmic laser system of claim 1, further comprising:
   a housing, configured to contain at least the objective lens of the optical system; and
   a patient interface device mounted on the housing, wherein the reflective surface is a surface of a lens of the patient interface device.

6. The ophthalmic laser system of claim 1, wherein the optical system includes a beam splitter disposed to guide a portion of the laser beam from the laser device to the objective lens and to guide a portion of the back-reflected laser beam from the objective lens to the imaging sensor.

7. The ophthalmic laser system of claim 1, wherein the optical system is free of any lens between the objective lens and the imaging sensor.

8. A method implemented in an ophthalmic laser system for measuring a laser focal spot size, comprising:
   mounting a reflective surface on a housing of the ophthalmic laser system and disposed in front of an objective lens of the ophthalmic laser system, the reflective surface being a planar surface other than a surface of an eye of a subject;
   by a laser device of the ophthalmic laser system, generating a laser beam;
   by the objective lens of the ophthalmic laser system, focusing the laser beam to a focal spot and scanning the focal spot in a depth direction within a predetermined depth range, the depth direction being parallel to an optical axis of the objective lens;
   by the objective lens, focusing a reflected portion of the laser beam that has been reflected by the reflective surface to form a back-reflected beam;
   by a two-dimensional imaging sensor of the ophthalmic laser system, receiving the back-reflected beam and capturing a plurality of images of the back-reflected beam while the focal spot is scanned within the depth range;
   by a controller of the ophthalmic laser system, analyzing the plurality of captured images to measure a smallest light spot size among the plurality of captured images; and by the controller, calculating a size of the focal spot of the laser beam using the measured smallest light spot size and a predetermined magnification factor.

9. The method of claim 8, wherein the predefined depth range includes a depth located at an offset distance before the reflective surface, wherein the offset distance is a fixed value determined by a focal length of the objective lens and a length of an optical path from the imaging sensor to the objective lens.

10. The method of claim 8, wherein the predetermined magnification factor is fixed value determined by a focal length of the objective lens and a length of an optical path from the imaging sensor to the objective lens.

11. The method of claim 8, wherein the step of analyzing the plurality of captured images to measure a smallest light spot size includes measuring a light spot size in each captured image by measuring a full width at half maximum of a two-dimensional light intensity profile in the captured image.

12. The method of claim 8, further comprising:
by a beam splitter of the ophthalmic laser system, guiding a portion of the laser beam from the pulsed laser to the objective lens and guiding a portion of the back-reflected beam from the objective lens to the imaging sensor without passing through any lens between the objective lens and the imaging sensor.

13. The method of claim 8, wherein the reflective surface is a surface of a patient interface device.

\* \* \* \* \*